United States Patent
Ritter (10) Patent No.: US 10,773,007 B2
(45) Date of Patent: Sep. 15, 2020

(54) BLOOD TREATMENT MACHINE COMPRISING SOS GENERATOR AND DISINFECTION METHOD

(71) Applicant: B. BRAUN AVITUM AG, Melsungen (DE)

(72) Inventor: Kai-Uwe Ritter, Melsungen (DE)

(73) Assignee: B. Braun Avitum AG, Melsungen (DE)

(*) Notice: Subject to any disclaimer, the term of this patent is extended or adjusted under 35 U.S.C. 154(b) by 48 days.

(21) Appl. No.: 16/206,209

(22) Filed: Nov. 30, 2018

(65) Prior Publication Data

US 2019/0192756 A1 Jun. 27, 2019

(30) Foreign Application Priority Data

Dec. 22, 2017 (DE) .................. 10 2017 131 104

(51) Int. Cl.
*A61M 1/16* (2006.01)
*A61L 2/04* (2006.01)
*A61L 2/18* (2006.01)

(52) U.S. Cl.
CPC .......... *A61M 1/169* (2013.01); *A61M 1/1686* (2013.01); *A61M 1/1688* (2014.02); *A61L 2/04* (2013.01); *A61L 2/18* (2013.01); *A61L 2202/24* (2013.01); *A61M 1/1682* (2014.02)

(58) Field of Classification Search
CPC .. A61M 1/169; A61M 1/1686; A61M 1/1682; A61M 1/1688; A61L 2/04; A61L 2/18; A61L 2202/24
See application file for complete search history.

(56) References Cited

U.S. PATENT DOCUMENTS

| 6,051,188 | A | 4/2000 | Spickermann |
| 6,379,617 | B1 | 4/2002 | Spickermann |
| 2012/0251631 | A1 | 10/2012 | Alimi et al. |

FOREIGN PATENT DOCUMENTS

| DE | 19640840 A1 | 4/1998 |
| DE | 202011105738 U1 | 12/2012 |

OTHER PUBLICATIONS

European Examination Report for European Application No. 18209392.2, dated May 16, 2019 with translation, 12 pages.
German Search Report for German Application No. 10 2017 131 104.1, dated Jul. 24, 2018, with English translation—14 pages.

*Primary Examiner* — John Kim (57) ABSTRACT

An extracorporeal blood treatment machine, preferably a dialysis machine, including a fluid circuit, preferably a dialysis fluid circuit, and a disinfectant supply line including an SOS generator integrated in the blood treatment machine which can be selectively connected to the fluid circuit by the disinfectant supply line and is adapted to provide a superoxidized solution or SOS for disinfection of the fluid circuit from dialysis concentrate and osmotic water, and a method for disinfection of an extracorporeal blood treatment machine.

12 Claims, 5 Drawing Sheets

BLOOD TREATMENT MACHINE COMPRISING SOS GENERATOR AND DISINFECTION METHOD

CROSS REFERENCE TO RELATED APPLICATIONS

This application claims priority to German application DE 10 2017 131 104.1 filed Dec. 22, 2017, the contents of such application being incorporated by reference herein.

FIELD OF THE INVENTION

The present invention relates to an extracorporeal blood treatment machine comprising an integrated SOS generator as well as an improved method for disinfecting extracorporeal blood treatment machines.

BACKGROUND OF THE INVENTION

For chronical dialysis in a center, dialysis machines are used successively by plural patients. Therefore, germs have to be prevented from being transmitted from one patient to the other. Thus, today in most cases hot disinfection of the dialysis fluid circuit is carried out between two dialysis treatments.

Depending on the apparatus variant and the manufacturer, the duration of the total process ranges from about 25 to 40 minutes. Such process is substantially composed of three phases:
- a heating phase, wherein disinfecting fluid, e.g. water, is heated until about 85° C. are reached, which generally takes about 15 minutes,
- a disinfection phase of approx. 15 minutes during which the different flow paths of the dialysis fluid circuit to be disinfected are rinsed with the disinfecting fluid and
- a phase during which the system is flushed and cooled, which again takes approx. 10 minutes.

Alternatively or additionally, chemical cold disinfections of the dialysis fluid circuit and of the dialysis machine are carried out. For this purpose, for example hypochlorite or peracetic acid are applied. This type of disinfection is carried out e.g. on a weekly basis only.

Said two disinfection methods entail several drawbacks. The current hot disinfection process requires high expenditure of time and energy, for example.

Furthermore, for the chemical disinfection for example additional chemicals such as citric acid, hypochlorite or peracetic acid are required. This incurs additional costs and, in addition, said chemicals have to be handled. This does not only entail increased efforts but further results in a plurality of potential sources of error. For instance, due the fact that the container holding disinfectant or decalcifier, e.g. citric acid, usually remains connected to the dialysis machine, there is the risk of such agent being sucked during treatment. For preventing this risk comprehensive protective measures are required on the apparatus side. Furthermore, for example citric acid, when being spilled, is very sticky and etching.

It is another drawback of chemical disinfection that the conductivity of some agents is within the range of the conductivity of concentrates which are required for conditioning dialysis fluid so that it cannot be safely identified whether a decalcifier canister has inadvertently been connected instead of the appropriate concentrate.

Moreover, the required chemicals are partially very aggressive and attack primarily stainless steels, particular plastic and ceramic materials. This is potentially resulting in corrosion of system components, which requires the use of high-quality materials.

Alternative disinfectants the use of which is known in dentistry, for example, are super-oxidized solutions (SOS: "super-oxidized solution" or SOW: "super-oxidized-water").

SOS are solutions that are produced by electro-chemical processes, especially electrolysis, from water and salts (e.g. sodium or potassium chloride). Accordingly, for example sodium hydroxide and hypochlorous acid as well as chlorine radicals are produced. An SOS as disinfecting solution shows excellent disinfecting results and attacks single-cell organisms, especially fungi, bacteria, viruses and spores, whereas multi-cell organisms such as human tissue are/is not attacked.

Moreover, SOS offer further advantages: They are stable solutions, are not corrosive and generally act quickly, can be pH-neutral to acid and can have a shelf life of up to one year. The starting substances for the production of SOS are inexpensive and the final product is environmentally friendly.

DESCRIPTION OF THE RELATED ART

A hot disinfection function as afore-described is integrated, for example, in the dialysis machine 4008S classix by Fresenius Medical Care. Another example of a hot disinfection system is Aquaboss by B. Braun which enables complete flow free from dead space through the entire dialysis fluid circuit or ring line system and in which a flow heater produces hot water only as needed.

During the disinfection process, the machine cannot be used. At best, the blood hose system can be activated for the next patient. Thus, the disinfection process is a determining factor for the time interval between two treatments.

SOS which at present are commercially available on the market are, for example, Sterilox, Microcyn or EnviroNize Anolyte, for which generators, such as the EnviroLyte Generator by EnviroNize, are available on the market.

SUMMARY OF THE INVENTION

As a consequence, it is an object of the invention to optimize the process of disinfection of an extracorporeal blood treatment machine, preferably a dialysis machine, as regards the clinical steps and the material consumption so that drawbacks such as afore-mentioned can be avoided. It is aimed at minimizing the time required for a disinfection process.

This object is achieved, according to aspects of the invention, in that an SOS generator for preparing SOS as an alternative disinfection solution is integrated into an extracorporeal blood treatment machine, i.e. is a fixed component of the hydraulic/fluid system thereof. In accordance with the invention, it was found that an SOS can be prepared also on the basis of acid dialysis concentrate. The SOS generator may be a commercially available SOS generator, such as the SOS generator described in the foregoing within the scope of prior art.

More exactly speaking, the afore-described object is achieved by an extracorporeal blood treatment machine, preferably a dialysis machine, in which an SOS generator is integrated. The extracorporeal blood treatment machine includes a fluid circuit (ring line), preferably a dialysis fluid circuit, and a disinfectant supply line which is connected to the fluid circuit and can be selectively released/opened/ unlocked, thus allowing the SOS generator to be selectively connected to/fluid-communicated with the fluid circuit. The SOS generator is adapted to prepare or, respectively, provide SOS for disinfection of the fluid circuit from dialysis concentrate and osmotic water which is available/stored at the extracorporeal blood treatment machine, where appropriate.

Further, during idle times of the blood treatment system the SOS is prevented from being drained after a disinfection and thus the SOS remains within the fluid circuit and possibly, in lines connected thereto. In this case, draining and flushing (i.e. completing the disinfection process) of the SOS is carried out before the extracorporeal blood treatment machine starts operation again, for example before a first treatment on the following day. This substantially corresponds to a deceleration of the disinfection process between the action and the draining of the SOS by an additional time period which substantially corresponds to the idle time. Alternatively or additionally, the SOS generator is adapted to automatically fill the fluid circuit, as well as lines preferably connected to the fluid circuit, directly before idle times of the blood treatment system.

This application is possible because SOS is not corrosive. Especially with longer idle times of the blood treatment machine such as overnight, this aspect of the present invention is advantageous. When, after a disinfection process, the SOS is retained in the fluid circuit and, where appropriate, in the connected lines, a repeated contamination is almost excluded and the repeated start of operation of the extracorporeal blood treatment machine is accelerated. Automatic filling of the disinfection fluid circuit and, where appropriate, of the connected lines can be carried out even without a preceding disinfection process which includes action of SOS (e.g. by circulating or rinsing the SOS), draining and flushing the SOS into/out of the fluid circuit. In this case, the growth of germs occurring during the idle time is strongly reduced. Thus, even before the next use, e.g. on the following day, an uncomplicated disinfection process is sufficient.

Feed lines for dialysis concentrate and osmotic water to the SOS generator may be connected to the same source or sources for osmotic water and electrolytes or, respectively, dialysis concentrate which also serve for providing fresh dialysis fluid during extracorporeal blood treatment.

A blood treatment machine according to aspects of the invention may be a hemodialysis, hemofiltration or hemodiafiltration machine. In the case of an open fluid circuit, the disinfectant supply line should advantageously be connected to the inlet of the open fluid circuit, wherein the inlet is, for instance, a port for feeding fresh dialysis fluid or components thereof to the fluid circuit. In a closed fluid circuit, the SOS generator can basically be arranged at/connected to each site of the fluid circuit by the disinfectant supply line, wherein possibly it has to be observed that several portions or units of the fluid circuit such as the dialysis filter/the hollow-fiber filter module can be short-circuited or bypassed by a bypass line. It is equally possible that the fluid circuit, which is an open fluid circuit during a dialysis treatment, is short-circuited during a disinfection process by short-circuiting the inlet (e.g. the port for supplying fresh dialysis fluid) and the outlet (e.g. a port for used dialysis fluid) thereof so that the SOS can circulate in the fluid circuit. Within the scope of a disinfection process, the SOS is filled into the fluid circuit (and, where required, bypass lines as well as, where required, other lines fluid-communicated with the fluid circuit), is let act and finally drained and flushed. Acting may include stagnant action of SOS, rinsing with SOS and/or, especially in a fluid circuit closed during the disinfection process, circulating SOS as well as combinations therefrom, and hereinafter it will altogether be referred to as "acting". The SOS is preferably flushed with fresh dialysis fluid or permeate from the ring line/the fluid circuit. Furthermore, the SOS generator may be in the form of a pump or alternatively an additional/separate pump (e.g. dosing pump) may be arranged in the disinfectant supply line so as to pump the SOS into the fluid circuit.

Acid dialysis concentrate which is suited for preparing SOS has a high salt content of more than 200 g/l NaCl. Said dialysis concentrate is required in large quantities in a dialysis center and thus is provided at the blood treatment machine anyway and/or is made available via a central supply. This is equally true for osmotic water. Thus, during disinfection of extracorporeal blood treatment machines advantageously disinfectants which are expensive and/or complicated to handle can be largely dispensed with, and the running costs incurred both by the disinfectants per se and by complex safety measures can be significantly reduced. Nevertheless, it is imaginable to optionally provide additional ports for said disinfectants so that the blood treatment machine can be (externally) disinfected, in the case of emergency, even if the SOS generator is defective, and can subsequently be used for dialysis. It is equally imaginable to provide external and, respectively, additional ports for water and common salt solution at the SOS generator. Furthermore, the dialysis fluid system/fluid circuit of the blood treatment machine according to aspects of the invention can be significantly simplified and the energy required (and possibly the time required) can be reduced, as the disinfection takes place at normal temperature. In addition, the shelf-life of further components of the fluid circuit, especially a dialysis fluid filter, is increased, as they are not subjected to any heat load and are not attacked by the SOS. Still, it is possible to slightly pre-heat SOS, where necessary, so as to further increase a disinfection performance of the SOS. In a blood treatment machine according to aspects of the invention, a disinfection process can be easily automated and is carried out quickly. Disinfection can be carried out within few minutes, which is especially due to the fact that heating and cooling operations are dispensed with.

Generally considered, the use of an SOS generator for disinfection of the blood treatment machine integrated in the blood treatment machine as a fixed component helps to significantly increase the safety of the system as well as the operation and functionality thereof and to reduce costs.

In accordance with a preferred aspect of the present invention, the fluid circuit includes a water processing portion, preferably a reverse-osmosis portion. The SOS generator may be selectively connected to the fluid circuit by a water drain line or water tapping line downstream of the water processing portion, with respect to the flow direction of the dialysis fluid or the disinfection fluid in the fluid circuit.

In other words, the osmotic water required for preparing the SOS is supplied to the SOS generator directly by the water processing portion of the blood treatment machine. Said water processing portion is used in plural extracorporeal blood treatment machines for processing dialysis fluid and consequently is a portion already present in a common extracorporeal blood treatment machine which is temporarily converted for disinfecting the system. This allows to dispense with additional lines or containers. It is noted that SOS must not get in contact with reverse-osmosis filters of a water processing portion and the circulation of SOS in the fluid circuit as well as the flushing after disinfection thus must not take place via said water processing portion. Where necessary, a bypass line is provided to bypass the SOS around the water processing portion.

In accordance with another preferred aspect of the present invention, the water drain line or water tapping line is provided for tapping a partial flow of the osmotic water. Said partial flow is supplied to the SOS generator and serves for preparing SOS. The SOS generated by the SOS generator is guided, within the scope of a selected disinfection process, into the fluid circuit (preferably without any additional heating), according to another preferred aspect of the invention through a metering pump disposed at the disinfectant supply line.

Said partial flow system enables the SOS generator as well as a metering pump, where appropriate, to be designed and dimensioned to be smaller, as only about 10% of the total treatment volume are required to generate sufficient SOS for a disinfection. A variable-displacement pump such as a reciprocating piston pump, peristaltic pump, diaphragm pump or gear-type pump can be employed as metering pump.

In accordance with a preferred aspect of the present invention, downstream of the SOS generator in the fluid circuit a sensor is provided which is adapted to monitor the freedom from chlorine outside a disinfection process and/or by which during a disinfection process the target concentration of SOS in the fluid circuit is controllable (by a control/regulating unit). For controlling the target concentration, a metering pump according to any one of the preceding preferred aspects of the invention may be provided, but also the SOS generator may be controlled so as to specifically prepare a particular quantity of SOS.

Said sensors may be sensors which are different from each other and are separated from each other; however, also one single sensor which is utilized for monitoring the freedom from chlorine and/or the control of the SOS target concentration may be used. It is imaginable, for example, for controlling the target concentration to combine the sensor with a metering pump according to a preceding preferred aspect of the invention or to drive the SOS generator itself in response to the sensor data. The sensor or, respectively, sensors preferably are sensors suited for measuring free chlorine, total chlorine or chlorine dioxide. Accordingly, known sensors such as Chloromax CC142D by Endress-Hauser may be employed. Basically, the sensors can be disposed everywhere in the fluid circuit or in lines connected to the latter and accessible to SOS, but an arrangement within the fluid circuit directly behind the port for the disinfectant supply line or in the disinfectant feed line itself is of advantage. When the sensor for monitoring the freedom from chlorine is used for measuring the SOS concentration during flushing at the end of a disinfection process, use at a portion of the fluid circuit or of lines connected thereto, where appropriate, is imaginable, in which portion the flow is irregular and, respectively, a fluid could be backed up. It is also imaginable to use the sensor for monitoring the freedom from chlorine in lines which should not be penetrated by SOS, such as a port of the water processing portion, for example.

According to a preferred aspect of the present invention, preferably upstream of sensitive units, preferably of the water processing portion, a protective unit is provided for protecting said units against contact with the SOS.

Said protective unit is adapted to detect SOS and to interrupt transferring of a fluid containing SOS. To this end, for example at the sensitive units a sensor detecting the presence of SOS at one of said sensitive units is provided. When SOS is present (i.e. for example when a concentration of SOS is exceeded), the flow of the fluid containing SOS is interrupted in the direction of the sensitive units, preferably by interrupting a hardware safety chain or generating a BUS signal and transmitting the same to a controller unit which switches a valve, e.g. a 3/2-way valve so as to bypass the fluid containing SOS into a drain. Accordingly, for example one of the sensors for monitoring the freedom from chlorine according to a preceding preferred aspect of the invention may be used for detecting SOS. Advantageously, said system can be employed for the protection of reverse osmosis filters of the water processing portion which must not get into contact with SOS. The protective unit is preferably provided upstream of the sensitive units, but it may also be disposed additionally downstream thereof, for example, so as to inhibit backflow of SOS. Alternatively, for this purpose also valves inhibiting return flow may be provided.

In accordance with a preferred aspect of the present invention, on the outside of the extracorporeal blood treatment machine a discharge port, preferably a cock, connected to the SOS generator is provided. Said cock is accessible for a user and serves for making SOS available as disinfectant to the user.

The discharge port (tap cock) may be manually operable and/or may open and close automatically, for example depending on whether there is something connected thereto or held thereunder. The SOS dischargeable from said discharge port is primarily provided for surface disinfection. The surfaces may be both surfaces of the blood treatment machine and surfaces that are independent thereof. However, also different applications are imaginable such as e.g. for disinfecting a patient's skin before placing a shunt. The discharge port may be connected to a hose, for example so as to guide SOS specifically to surfaces to be disinfected. As an alternative, the discharge port may also be directly accessible so as to soak e.g. disinfecting tissues with SOS. Advantageously, in this way SOS can also be used for disinfecting components outside the fluid circuit or even outside of the blood treatment machine, thus allowing to considerably reduce the required quantity of other disinfectants. Advantageously, the discharge port cannot only be used during a disinfection process but also during a dialysis treatment, for which purpose the SOS generator can be pinched off the fluid circuit, for example, or a reservoir that has been filled by the SOS generator before can be used.

In accordance with a preferred aspect of the present invention, the fluid circuit may be an open circuit, with the SOS generator being connected to ports for dialysis concentrate and osmotic water.

This constitutes the simplest variant of the system according to aspects of the invention and can be easily retrofitted, where necessary, to existing blood treatment machines.

Another imaginable (preferred) aspect of the present invention resides in the fact that the fluid circuit and/or sensitive units of the blood treatment machine can be short-circuited so as to circulate SOS with a circulation pump inside the fluid circuit. In this way, a partial flow can repeatedly be circulated via the SOS generator, thus causing the content of SOS in the fluid circuit to be increased. The SOS generator may be configured to be smaller in this case. However, as a result the disinfection time and the expenditure on apparatuses are increased.

Possible variations and configurations that have already been discussed within the scope of the description of the extracorporeal blood treatment machine are also applicable to corresponding elements of the method described below and will not repeatedly be described.

Furthermore, the object is achieved by a method of disinfecting a fluid circuit (ring line), preferably a dialysis fluid circuit, of an extracorporeal blood treatment machine comprising the following steps of:

supplying or providing/storing dialysis concentrate and osmotic water to/at an SOS generator integrated in the extracorporeal blood treatment machine;

generating super-oxidized solution or SOS by the SOS generator;

filling the SOS into the fluid circuit;

acting of the SOS during a pre-established disinfection period; and draining and flushing the SOS after expiry of the disinfection period until a concentration of the (residual) SOS present in the fluid circuit falls below a concentration limit.

The method further comprises the following steps of:

establishing an idle time of the blood treatment apparatus; and filling the fluid circuit and preferably lines connected to the fluid circuit with SOS directly before the idle time and performing a disinfection process (including acting, draining and flushing of the SOS) and, respectively, the disinfection method according to aspects of the invention before the extracorporeal blood treatment machine starts operation again; or preventing SOS from being drained after disinfection (i.e. after acting of the SOS in the fluid circuit), directly before the idle time and completing the disinfection process (draining and flushing of the SOS) before the extracorporeal blood treatment machine starts operation again.

The start of operation of the extracorporeal blood treatment machine again is understood to be an end of the idle time, i.e. before a new dialysis treatment is carried out. Preferably, the disinfection process is carried out and the disinfection process is completed, respectively, directly before a new dialysis treatment.

In this context, acting may include both stagnant acting of SOS, rinsing with SOS and/or, especially in a closed fluid circuit, circulating of SOS as well as a combination thereof. The disinfection process adapted to be implemented by way of this method preferably takes place at room temperature. Thus, especially no heating of the disinfection fluid is required so that consequently the dialysis fluid circuit need not be cooled following a disinfection so as to be usable for a dialysis treatment. This results in significantly shorter process times than during hot disinfection, in particular as the cooling operation is omitted. This method can be initiated and performed both manually and by automation. Furthermore, apart from the disinfection period optionally also a required quantity of SOS may be predetermined so that the SOS generator prepares specifically only the quantity of SOS required for one disinfection process. As an alternative it is also imaginable that the SOS generator produces the required quantity of SOS for a particular treatment period, for example for one day, in advance and keeps it in a reservoir.

In accordance with a preferred aspect of the present invention, the method further comprises a step in which the SOS generator is supplied with dialysis fluid for preparing SOS via a water drain line which is connected to a water processing portion for used dialysis fluid (and, respectively, for providing osmotic water), said water processing portion being interconnected (connected in series or in parallel) in the (now closed) fluid circuit.

According to a preferred aspect of the present invention, the method further comprises the following steps of:

draining a flow, preferably a partial flow, of osmotic water from the fluid circuit through the water drain line; and supplying the SOS from the SOS generator to the fluid circuit, preferably via a metering pump.

Said steps according to the two afore-described preferred aspects are applied to an embodiment of the invention in which the SOS generator obtains the osmotic water required for preparing SOS directly from the fluid circuit.

According to a preferred aspect of the present invention, the method further comprises a step in which a target concentration of SOS in the fluid circuit is controlled with the aid of a sensor by a control/regulating unit. Alternatively or additionally, a sensor for monitoring the freedom from chlorine outside a disinfection process may be provided.

The target concentration may be controlled especially dynamically on the basis of SOS concentration data of the sensor and may be adjusted with the aid of a metering pump. Alternatively, the SOS generator may be set to produce a particular quantity of SOS. Furthermore, it is also possible to calculate the target concentration once and to adjust the same by way of the metering pump or the determination of the SOS quantity instead of dynamically controlling the same.

According to a preferred aspect of the present invention, the method further comprises the following steps of:

Identifying SOS by a sensor of a protective unit which is arranged (preferably upstream) directly next to sensitive units, preferably a water processing portion, in the fluid circuit; and activating the protective unit which prevents the SOS from being transferred to the sensitive units and especially initiates draining of the SOS.

BRIEF DESCRIPTION OF THE DRAWINGS

The invention is best understood from the following detailed description when read in connection with the accompanying drawings. Included in the drawings are the following figures.

DETAILED DESCRIPTION OF THE PREFERRED EMBODIMENTS

Figure 1:
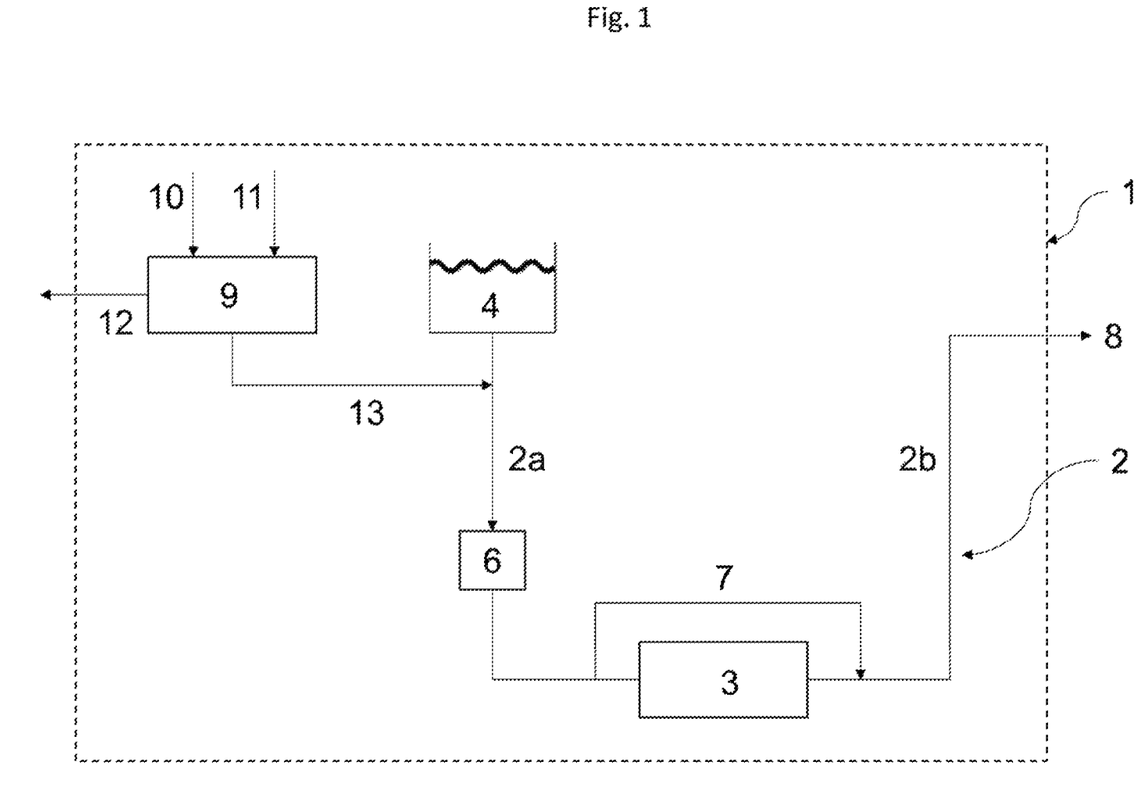
FIG. 1 shows a schematic diagram of an embodiment with an open fluid circuit.

FIG. 1 illustrates a schematic diagram of a simple embodiment of a dialysis fluid side of an extracorporeal blood treatment machine 1 according to aspects of the invention. A blood side of the extracorporeal blood treatment machine 1 is not depicted in order to facilitate representation. For the same purpose, the representation of the dialysis fluid side and, respectively, of the fluid circuit 2 is further reduced so that merely elements of a fluid circuit 2 required for illustrating the invention are shown. It is understood that, apart from said shown elements, the extracorporeal blood treatment machine includes a blood circuit which can be connected during dialysis treatment to a patient's vessels via a shunt and may include diverse components such as a blood pump, pressure and temperature sensors and an air trapping, wherein dialysis fluid guided through the fluid circuit 2 and a patient's blood guided through the blood circuit are guided through a hollow-fiber filter module 3 within the scope of a dialysis treatment for the exchange of uremic toxins as well as, where necessary, of electrolytes and water between blood and dialysis fluid in a counter flow principle. It is further understood that also a fluid circuit 2 includes further elements such as electrolyte feed lines, mixers, pumps, sensors and valves. Said elements, which are not shown, are known from the state of the art and will not be described in more detail hereinafter. This is equally applicable to all embodiments of the invention described hereinafter.

The terms "downstream" and "upstream" are always relating to a direction of flow of dialysis fluid in the fluid circuit 2 during a dialysis treatment and, respectively, to a direction of flow of disinfectant in the fluid circuit 2 during a disinfection process.

The extracorporeal blood treatment machine 1 shown in FIG. 1 includes an open fluid circuit/a ring line 2, preferably a dialysis fluid circuit. The latter has a port to at least one source (reservoir/feed line) 4, here shown simplified as a fluid container, for providing fresh dialysis fluid or, respectively, components thereof, such as osmotic water, which are mixed with electrolytes to form fresh dialysis fluid when they flow through a feed line portion 2a of the fluid circuit 2, preferably through mixing chambers arranged in the feed line portion 2a. The at least one source 4 may be, for example, a reservoir provided at/in the blood treatment machine or a port to a dialysis fluid source external to the blood treatment machine.

The source for fresh dialysis fluid 4 is connected to (fluid-communicated with) the feed line portion 2a of the fluid circuit 2. The feed line portion 2a includes a port for a disinfectant supply line 13 preferably directly downstream of the connecting site where the feed line portion 2a is fluid-communicated with the at least one source 4. Preferably directly downstream of the connecting site where the disinfectant supply line 13 is connectable or connected to the feed line portion 2a, a sensor 6 which is suited for measuring SOS, especially free chlorine, total chlorine or chlorine dioxide, and may serve for monitoring the freedom from chlorine (e.g. when flushing the SOS) and/or for setting an SOS target concentration in the fluid circuit 2 is disposed in the feed line portion 2a.

The feed line portion 2a is further fluid-communicated with a hollow-fiber filter module 3 downstream of the sensor 6. In said hollow-fiber filter module 3 during a dialysis treatment the exchange between dialysis fluid and blood takes place and during the disinfection process said hollow-fiber filter module may be short-circuited with the aid of a bypass line 7 for disinfecting the fluid circuit 2. During a disinfection process the bypass line 7 is fluid-communicated with the feed line portion 2a directly upstream of the hollow-fiber filter module 3 and is fluid-communicated with a drain line portion 2b of the fluid circuit 2 directly downstream of the hollow-fiber filter module 3, with the flow through the hollow-fiber filter module 3 being inhibited so that the SOS is bypassed around the hollow-fiber module 3. The inhibition of the flow through the hollow-fiber module 3 (separation of the fluid communication between the hollow-fiber module 3 and the fluid circuit 2) can be realized, for example, by stop valves or by removing the hollow-fiber filter module 3 preferably being in the form of a disposable.

The drain line portion 2b is adapted to drain dialysis fluid used during a dialysis treatment from the hollow-fiber filter module 3 and opens into a drain 8 for disposing of used dialysis fluid which can be disposed of in this way (via the drain line portion 2b and the drain 8). The drain may additionally be connected to a collecting container (not shown) for collecting used dialysis fluid. Furthermore, the drain line portion 2b and the drain 8 are configured to drain SOS during a disinfection process.

Furthermore, an SOS generator 9 is integrated in the extracorporeal blood treatment machine 1 (a fixed component of a hydraulic system internal to the blood treatment machine). Said SOS generator is fluid-communicated with feed lines for dialysis concentrate 10 and osmotic water 11 via which necessary components for preparing SOS are supplied to the SOS generator 9.

The SOS generator 9 includes a discharge port (tap port) 12 which enables fluid communication with the space surrounding the blood treatment machine 1 and which provides SOS also for use outside the blood treatment machine 1.

The SOS generator 9 is fluid-communicated with a disinfectant supply line 13 which is adapted to supply SOS prepared by the SOS generator 9 to the fluid circuit 2. To this end, the SOS generator 9 is optionally equipped with a pump or, alternatively, an additional (separate) pump is disposed in the disinfectant supply line 13. Thus, the disinfectant supply line 13 can be selectively connected to (fluid-communicated with) an inlet of the open fluid circuit 2, i.e. directly downstream of the connecting site where the feed line portion 2a is fluid-communicated with the at least one source 4.

Figure 2:
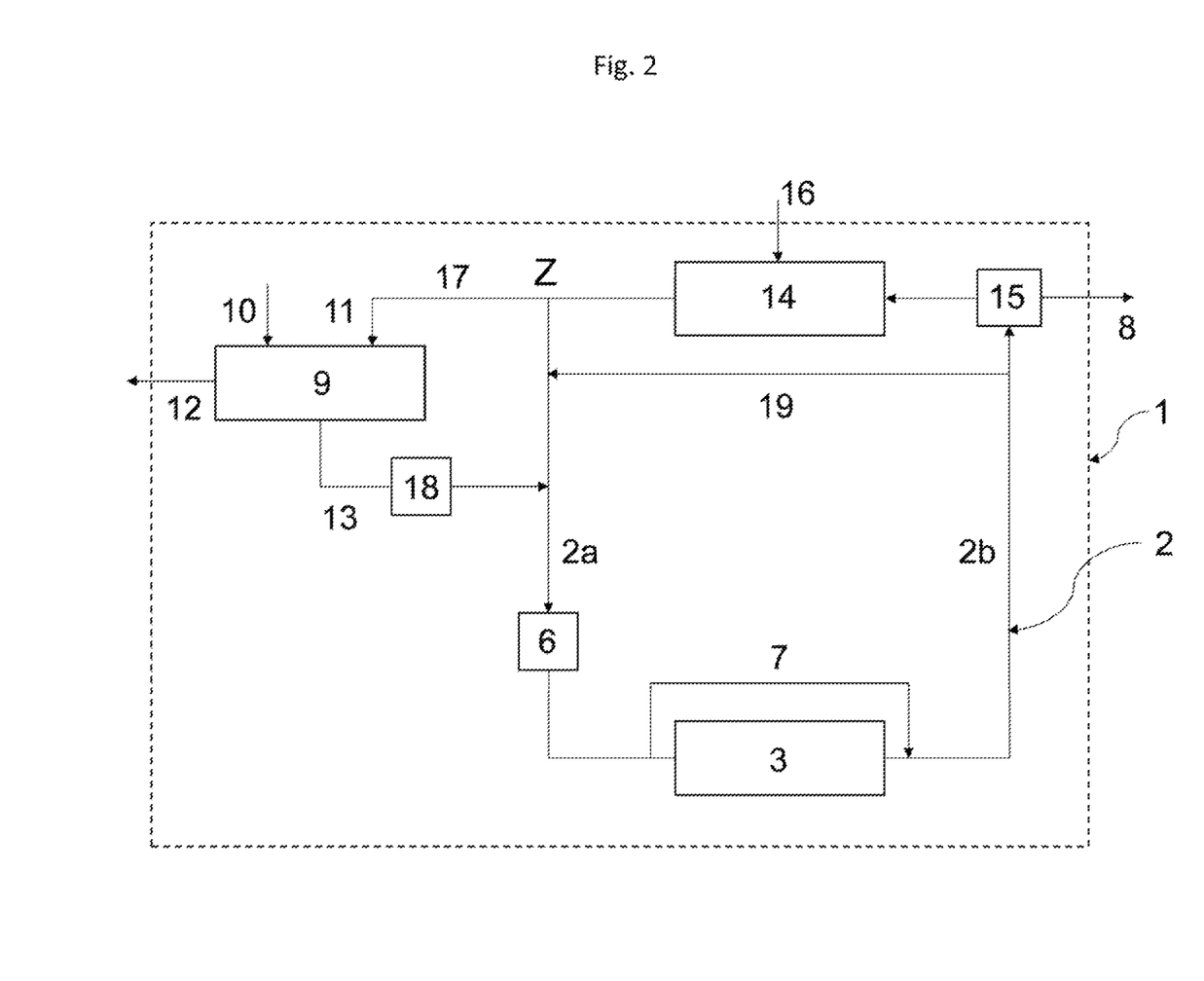
FIG. 2 shows a schematic diagram of a second embodiment with a closed fluid circuit.

FIG. 2 shows a second preferred embodiment of the extracorporeal blood treatment machine according to aspects of the invention which is based on the embodiment described before by way of FIG. 1. Accordingly, elements corresponding to each other are referenced by like reference numerals and are not repeatedly described.

Other than in the blood treatment machine shown in FIG. 1, in the embodiment according to FIG. 2 a closed fluid circuit 2 including a water processing portion 14 is provided which is adapted to provide/produce osmotic water by reverse osmosis.

During dialysis treatment, used dialysis fluid from the hollow-fiber filter module 3 is guided in the drain line portion 2b of the fluid circuit 2. The drain line portion 2b is fluid-communicated with or connectable to an inlet of the water processing portion 14 and directly upstream of the water processing portion 14 a protective unit 15 is arranged in the drain line portion 2b. Said protective unit 15 serves for protection of the water processing portion 14, especially by reverse osmosis filters contained in the same, especially during a disinfection process, and will later be described in detail. The used dialysis fluid drained from the hollow-fiber filter module 3 within the scope of a dialysis treatment is thus guided into the drain line portion 2b via the protective unit 15 at least partially into the water processing portion 14, where it is processed by reverse osmosis and serves for producing osmotic water. The water processing portion 14 additionally has a water supply line 16 which is adapted to supply/provide water for producing osmotic water to the water processing portion 14 additionally or alternatively to the used dialysis fluid.

The outlet of the water processing portion 14 branches at a branch Z into the feed line portion 2a of the fluid circuit 2 which leads to the inlet of the hollow-fiber filter module 3. The outlet of the water processing portion 14 at the branch Z further branches into a water drain line 17 which opens into the SOS generator 9 which in turn can be selectively fluid-communicated with the feed line portion 2a downstream to the branch Z via the disinfectant feed line 13 for carrying out a disinfection process. In the feed line portion 2a the sensor 6 for measuring an SOS concentration is provided directly behind the port for the disinfectant supply line 13. Furthermore, in the feed line portion 2a a mixing portion (not separately shown) is provided which is adapted to mix the osmotic water provided by the water processing portion 14 with electrolytes or, respectively, dialysis concentrate, and in this way to make available fresh dialysis fluid during a dialysis treatment. Furthermore, the feed line portion 2a is adapted to supply the fresh dialysis fluid to the hollow-fiber filter module 3.

During a disinfection process, the water drain line 17 is fluid-communicated with the feed line portion 2a at the branch Z directly downstream of the water processing portion 14. The water drain line 17 is further fluid-communicated with the SOS generator 9 and is adapted to supply a partial flow of osmotic water provided by the water processing portion 14 to the SOS generator 9, while the remaining osmotic water branches into the feed line portion 2a. The SOS generator 9 generates SOS from the osmotic water provided through the water drain line 17 and dialysis concentrate or, respectively, electrolytes provided through a feed line for dialysis concentrate 10. The SOS generator 9 is fluid-communicated with the disinfectant supply line 13. In the disinfectant supply line 13 a metering pump 18 is provided which pumps a metered quantity of SOS into the feed line portion 2a being fluid-communicated during the disinfection process with the disinfectant supply line 13, where the SOS mixes as partial flow with the osmotic water flowing in the feed line portion 2a. The sensor 6 measures an SOS concentration in the feed line portion 2a and outputs a concentration sensor signal on the basis of which the metering pump 18 is controllable so as to adjust a target concentration of SOS in the feed line portion 2a.

It is basically also imaginable to alternatively interrupt the fluid communication between the port for the water drain line 17 and the port for the disinfectant supply line 13 and to circulate, instead of a partial flow, the total flow via the SOS generator 9, wherein a metering pump 18 is not necessary and the concentration of SOS can be directly adjusted by the SOS generator 9.

In the embodiment shown in FIG. 2, during a disinfection process the bypass line 7 is provided which is a first bypass line and which can be selectively connected to (fluid-communicated with) the feed line portion 2a and to the drain line portion 2b so as to bypass SOS around the hollow-fiber filter module 3 and to couple the latter out of the fluid circuit 2. Furthermore, a second bypass line 19 can be fluid-communicated with the drain line portion 2b directly in front of/upstream of the protective unit 15 and, respectively, is fluid-communicated with the drain line portion 2b and with the feed line portion 2a, preferably upstream of the mixing portion, during a disinfection process. The second bypass line 19 is thus adapted to return the SOS from the drain line portion 2b into the feed line portion 2a and, in so doing, bypass the SOS around the water processing portion 14 and the protective unit 15. In this way, the SOS can be circulated in the fluid circuit 2.

The protective portion 15 which is arranged directly downstream of the site where the second bypass line 19 is connected to the drain line portion 2b includes a sensor which measures an SOS concentration, wherein upon exceeding a concentration limit the protective portion 15 interrupts the fluid circuit 2, bypasses especially fluid containing SOS to a drain 8 so that no fluid containing SOS can be transferred to the water processing portion 14.

Figure 3:
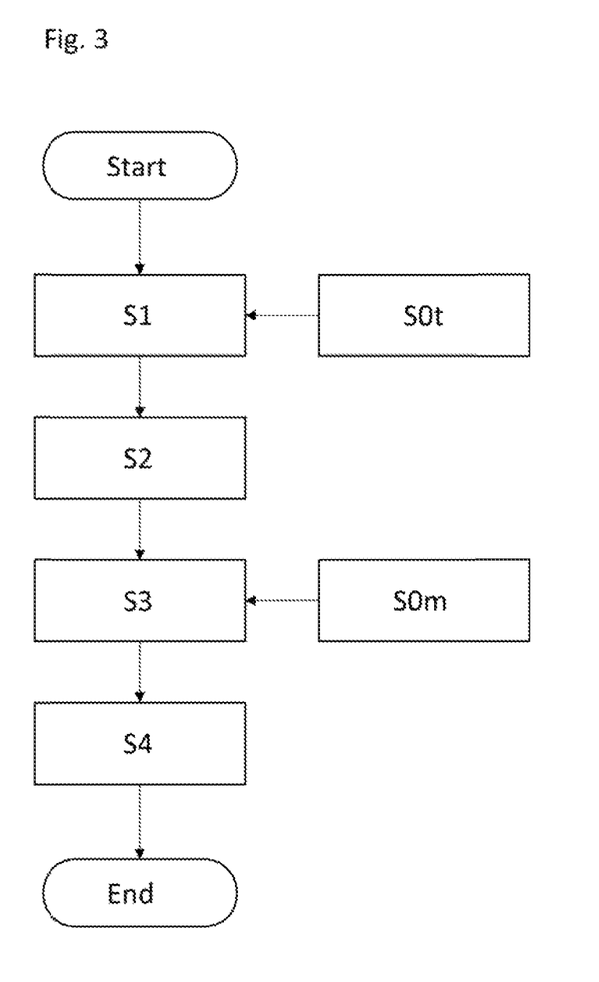
FIG. 3 shows a flow diagram for an example of the method according to aspects of the invention.

FIG. 3 illustrates a flow diagram for an example of a method according to aspects of the invention which is a disinfection process. Accordingly, the required disinfection time S0t and, where necessary, the required quantity of SOS S0m are pre-established. In a first step S1, a possibly pre-established quantity of SOS is generated. Subsequently, in a second step S2, the disinfection fluid circuit and, where necessary, the lines connected thereto are filled with SOS. In a third step S3, the SOS is let act during the predetermined disinfection time. In a fourth step S4, the SOS is drained and flushed until a concentration of the SOS established by a sensor falls below a predetermined limit.

Figure 4:
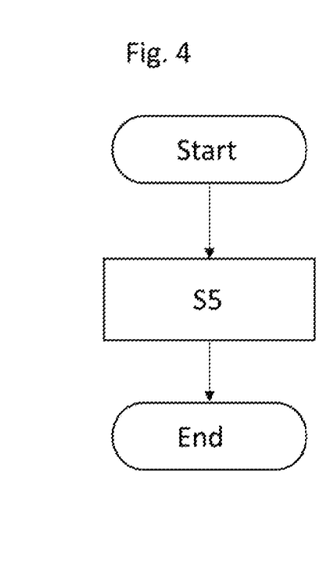
FIG. 4 shows a flow diagram for a partial method according to aspects of the invention for an embodiment of the invention in which the SOS generator obtains osmotic water from the fluid circuit.

FIG. 4 shows a flow diagram for a step S5 of a partial method according to aspects of the invention, for an embodiment in which the SOS generator obtains osmotic water from the fluid circuit 2. In step S5, the SOS generator 9 is connected to the fluid circuit 2 through a water drain line 17.

Figure 5:
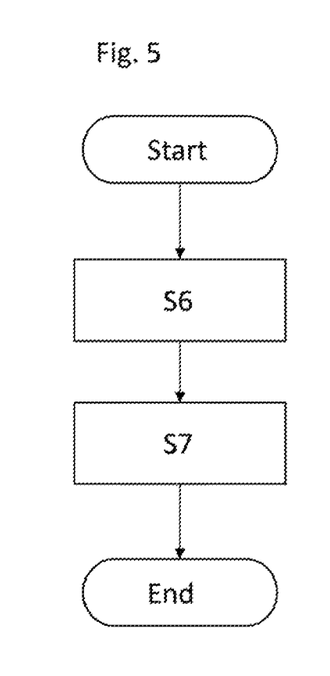
FIG. 5 shows a flow diagram for a partial method according to aspects of the invention for a preferred aspect of the embodiment according to FIG. 4.

FIG. 5 shows a flow diagram for steps of a partial method according to aspects of the invention, wherein, in step 6, a partial flow of osmotic water is guided from the fluid circuit 2 through the water drain line 17 to the SOS generator 9 and, in step S7, the SOS generated by the SOS generator 9 is guided into the fluid circuit 2, preferably through a metering pump 18

Figure 6:
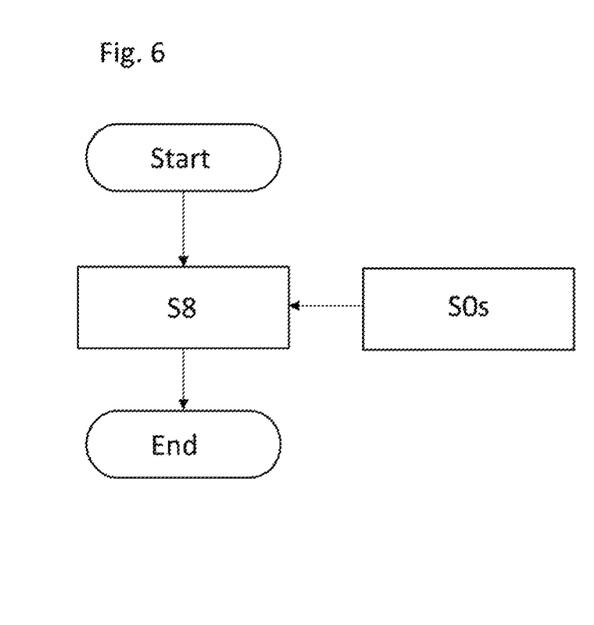
FIG. 6 shows a flow diagram for a partial method according to aspects of the invention for an embodiment of the invention, with a metering pump for supply of SOS to the fluid circuit being provided.

FIG. 6 illustrates a flow diagram for steps of a partial method according to aspects of the invention, wherein, in step S0s, an SOS concentration in the fluid circuit 2 is measured by way of a sensor and wherein, in step 8, a target concentration of SOS is adjusted, preferably by a metering pump 18, in the fluid circuit 2. This partial method can be used especially when the SOS is gener a partial flow principle in which a partial flow is discharged from the fluid circuit 2 and is supplied to the SOS generator and SOS prepared therefrom is supplied to the fluid circuit 2 again, preferably with the aid of a metering pump 18.

Figure 7:
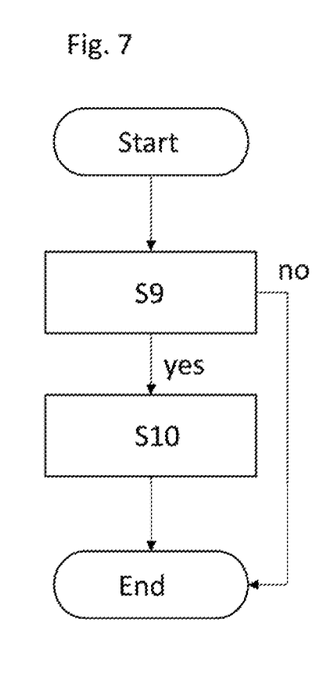
FIG. 7 shows a flow diagram for a partial method according to aspects of the invention for an embodiment of the invention, with a protective unit for protecting particular units against contact with SOS is provided.

FIG. 7 shows a flow diagram for steps of a partial method according to aspects of the invention, wherein, in step S9, presence of SOS is identified upstream of sensitive units such as a water processing portion 14 by a sensor of a protective unit 15 and, in step S10, upon identifying presence of SOS the protective unit 15 is activated so as to divert the fluid containing SOS and, respectively, to inhibit further flow to the sensitive units.

Figure 8A:
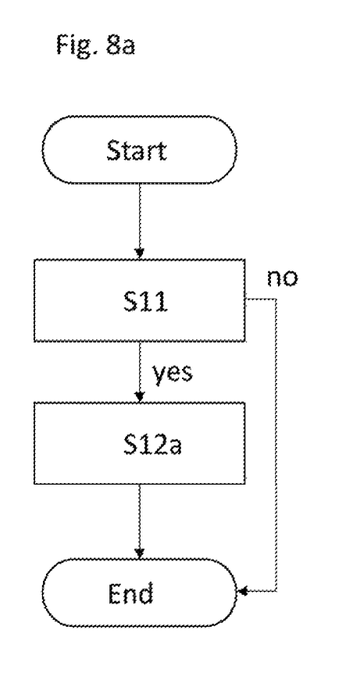
FIGS. 8a and 8b show flow diagrams for partial methods according to aspects of the invention ensuring that the fluid circuit is filled with SOS during an idle time.
Figure 8B:
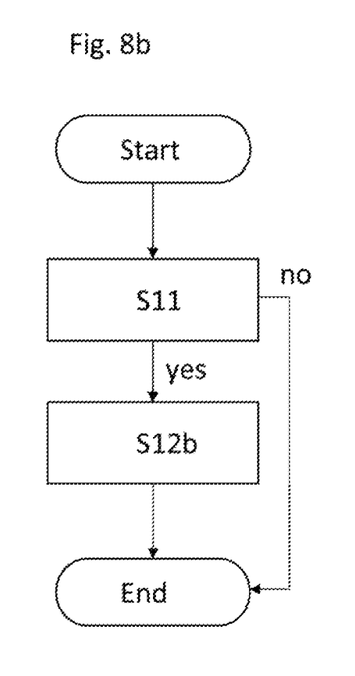

FIG. 8a and FIG. 8b show flow diagrams for steps of partial methods according to aspects of the invention which ensure that during an idle time the fluid circuit 2 is filled with SOS. In step S11 is established in each case whether an idle time of the extracorporeal blood treatment machine is upcoming. In the partial method according to FIG. 8a, in step S12a, upon establishing an idle time the fluid circuit 2 as well as lines connected thereto are filled with SOS directly before the idle time and/or after the last dialysis treatment. This partial method can also take place before a disinfection process has taken place, wherein a disinfection process may take place before the next use, for example on the following day. In the partial method according to FIG. 8b, in step S12b, on the other hand, upon establishing an idle time following a disinfection the draining and flushing of SOS is prevented and the disinfection process can be completed before the next use, for example on the following day.

The invention claimed is:

1. An extracorporeal blood treatment machine comprising:
a fluid circuit;
a disinfectant supply line connected to the fluid circuit and selectively releasable from the fluid circuit; and
a super-oxidize solution (SOS) generator integrated in the extracorporeal blood treatment machine is fluid-communicable with the fluid circuit through the disinfectant supply line and is adapted for providing a SOS from dialysis concentrate and osmotic water for disinfection of the fluid circuit;
wherein, during an idle time, the extracorporeal blood treatment machine is adapted to prevent SOS from being drained and flushed after disinfection, and further adapted to drain and flush the SOS before operation of the extracorporeal blood treatment machine is started again, and
wherein, the fluid circuit is an open circuit, with the SOS generator connected to ports for dialysis concentrate and osmotic water.

2. The extracorporeal blood treatment machine according to claim 1, wherein the SOS is guided into the fluid circuit after being metered through a metering pump provided at the disinfectant supply line.

3. The extracorporeal blood treatment machine according to claim 1, further comprising:
a sensor positioned downstream of the SOS generator in the fluid circuit, the sensor adapted to monitor a freedom of chlorine outside a disinfection process and/or a target concentration of the SOS in the fluid circuit is controllable based on readings of the sensor during a disinfection process.

4. The extracorporeal blood treatment machine according to claim 1, wherein on an outside of the extracorporeal blood treatment machine a discharge port connected to the SOS generator is provided which is accessible to a user and provides the user with the SOS as disinfectant.

5. An extracorporeal blood treatment machine comprising:
a fluid circuit;
a disinfectant supply line connected to the fluid circuit and selectively releasable from the fluid circuit; and
a super-oxidize solution (SOS) generator integrated in the extracorporeal blood treatment machine is fluid-communicable with the fluid circuit through the disinfectant supply line and is adapted for providing a SOS from dialysis concentrate and osmotic water for disinfection of the fluid circuit;
wherein the SOS in idle times of the extracorporeal blood treatment machine after disinfection is retained in the fluid circuit and the SOS is drained and flushed immediately before starting operation again; or
wherein the SOS generator is adapted to automatically fill the fluid circuit immediately before idle times of the extracorporeal blood treatment machine, with a disinfection process being carried out immediately before starting operation again, the extracorporeal blood treatment machine further comprising a protective unit upstream of sensitive units for protecting the sensitive units against contact with the SOS.

6. An extracorporeal blood treatment machine comprising:
a fluid circuit;
a disinfectant supply line connected to the fluid circuit and selectively releasable from the fluid circuit; and
a super-oxidize solution (SOS) generator integrated in the extracorporeal blood treatment machine is fluid-communicable with the fluid circuit through the disinfectant supply line and is adapted for providing a SOS from dialysis concentrate and osmotic water for disinfection of the fluid circuit;
wherein the SOS in idle times of the extracorporeal blood treatment machine after disinfection is retained in the fluid circuit and the SOS is drained and flushed immediately before starting operation again; or
wherein the SOS generator is adapted to automatically fill the fluid circuit immediately before idle times of the extracorporeal blood treatment machine, with a disinfection process being carried out immediately before starting operation again, wherein the fluid circuit is an open circuit, with the SOS generator connected to ports for dialysis concentrate and osmotic water.

7. A method for disinfection of a fluid circuit of an extracorporeal blood treatment machine according to claim 1, the method comprising the steps of:
supplying dialysis concentrate and osmotic water to an SOS generator integrated in the extracorporeal blood treatment machine;
generating the SOS by the SOS generator;
filling the fluid circuit with the SOS;
using the SOS during a pre-established disinfection period;
draining and flushing the SOS after expiry of the disinfection period until a concentration of residual SOS present in the fluid circuit falls below a concentration limit,
establishing an idle time of the extracorporeal blood treatment machine; and
filling the fluid circuit with the SOS immediately before the idle time and carrying out a disinfection process before the operation of the extracorporeal blood treatment machine is started again, or preventing SOS from being drained and flushed, when a subsequent idle time has been established, and draining and flushing the SOS before operation of the extracorporeal blood treatment machine is started again.

8. The method according to claim 7, further comprising the step of:
connecting the SOS generator to the fluid circuit via a water drain line which is connected to a water processing portion being interconnected in a closed fluid circuit.

9. The method according to claim 8, further comprising the steps of:
draining a flow of osmotic water from the fluid circuit through the water drain line and supplying the partial flow to the SOS generator; and
supplying the SOS from the SOS generator into the fluid circuit.

10. The method according to claim 7, further comprising the step of:
controlling a target concentration of the SOS in the fluid circuit using a sensor.

11. A method for disinfection of a fluid circuit of an extracorporeal blood treatment machine, the extracorporeal blood treatment machine comprising:
- a fluid circuit;
- a disinfectant supply line connected to the fluid circuit and selectively releasable from the fluid circuit; and
- a super-oxidize solution (SOS) generator integrated in the extracorporeal blood treatment machine is fluid-communicable with the fluid circuit through the disinfectant supply line and is adapted for providing a SOS from dialysis concentrate and osmotic water for disinfection of the fluid circuit;
- wherein the SOS in idle times of the extracorporeal blood treatment machine after disinfection is retained in the fluid circuit and the SOS is drained and flushed immediately before starting operation again; or
- wherein the SOS generator is adapted to automatically fill the fluid circuit immediately before idle times of the extracorporeal blood treatment machine, with a disinfection process being carried out immediately before starting operation again, the method comprising the steps of:
- supplying dialysis concentrate and osmotic water to an SOS generator integrated in the extracorporeal blood treatment machine;
- generating the SOS by the SOS generator;
- filling the fluid circuit with the SOS;
- using the SOS during a pre-established disinfection period;
- draining and flushing the SOS after expiry of the disinfection period until a concentration of residual SOS present in the fluid circuit falls below a concentration limit,
- establishing an idle time of the extracorporeal blood treatment machine;
- filling the fluid circuit with the SOS immediately before the idle time and carrying out a disinfection process before the operation of the extracorporeal blood treatment machine is started again, or preventing SOS from being drained and flushed, when a subsequent idle time has been established, and draining and flushing the SOS before operation of the extracorporeal blood treatment machine is started again;
- identifying the SOS by a sensor of a protective unit arranged in the fluid circuit; and
- activating the protective unit to prevent the SOS from being transferred to sensitive unit.

12. The method according to claim 11, wherein the activating step initiates draining of the SOS.

* * * * *